(12) United States Patent
Kawaji

(10) Patent No.: US 6,946,514 B2
(45) Date of Patent: Sep. 20, 2005

(54) ADHESIVE PREPARATION FOR EXTERNAL USE

(75) Inventor: Toshikuni Kawaji, Ohkawa-gun (JP)

(73) Assignee: Teikoko Seiyaku Co. Ltd., Kagawa (JP)

( * ) Notice: Subject to any disclaimer, the term of this patent is extended or adjusted under 35 U.S.C. 154(b) by 260 days.

(21) Appl. No.: 10/203,273

(22) PCT Filed: Nov. 29, 2000

(86) PCT No.: PCT/JP00/08441

§ 371 (c)(1),
(2), (4) Date: Aug. 8, 2002

(87) PCT Pub. No.: WO02/43711

PCT Pub. Date: Jun. 6, 2002

(65) Prior Publication Data

US 2003/0100852 A1   May 29, 2003

(51) Int. Cl.[7] ................................. C08L 9/06
(52) U.S. Cl. ...................... 524/575; 524/502
(58) Field of Search .................. 524/502, 575, 524/10

(56) References Cited

FOREIGN PATENT DOCUMENTS

| JP | 54-101420 | 8/1979 |
|---|---|---|
| JP | 56-039014 | 4/1981 |
| JP | 60-2253 | 1/1985 |
| JP | 4-321624 | 11/1992 |
| JP | 5-105630 | 4/1993 |
| JP | 6-024969 | 2/1994 |

*Primary Examiner*—Ling-Sui Choi
(74) *Attorney, Agent, or Firm*—Crowell & Moring LLP

(57) ABSTRACT

An external plaster using an aqueous hot melted type adhesive base material stably containing water-soluble drug having good drug releasability, so that bioavailability of the drug is enhanced, is provided. The aqueous hot melted type adhesive base material used in the external plaster comprising as essential components a styrene-isoprene-styrene block copolymer, an adhesive resin, an antioxidant, lanolin, and water.

38 Claims, No Drawings

ADHESIVE PREPARATION FOR EXTERNAL USE

TECHNICAL FIELD

The present invention relates to an external plaster using an aqueous hot melted type adhesive base material comprising lanoline and water as essential components, as well as a process producing thereof. More particularly, the present invention relates to an external plaster using water containing hot melted type adhesive base material having low irritation to skin in which crystallization of an active ingredient therein does not happen and has high bioavailability of the active ingredient.

BACKGROUND ART

For water containing aqueous external preparations, ointments, lotions, aqueous plasters, and the like have been proposed up to now. Among these external preparations, ointments and lotions have been considered less suitable for administration of an active ingredient containing therein continuously and in constant dosages and are also thought to be inconvenient since they may stick elsewhere other than the intended application site, and may sometimes soil the clothes at the time of administration.

Further, an aqueous plaster, though not associated with these problems, has a low adhesiveness and thus requires fixing means such as a strip of surgical tape so that it stays on flextion parts such as elbows and knees.

On the other hand, there has been non-aqueous adhesives preparation using natural or synthetic rubber as a base material or plaster using adhesive acrylate type resin as base material. These types of preparations have a strong adhesiveness and are thought to overcome the drawbacks of aqueous plasters.

However, it is difficult to dissolve an active ingredient in the non-aqueous adhesive base material when said active ingredient hardly dissolves in polyols, glycols, and esters, which are commonly used as a solvent for external plasters. Especially, addition of water-soluble drug causes many problems such as appearance of crystalline of the drugs in the base material, low percutaneous absorption of the drugs, and so on due to the low solubility of said drugs To solve these problems, for example, there has been proposed to use crotamiton as a solubilizer for the drugs in Japanese Patent Laid-Open Publication No. Hei 4-321624. However, it has been difficult heretofore, even with the help of the solubilizer, to obtain the non-aqueous adhesive base material that contains drugs in an amount sufficient to allow it to exert desired pharmacological effects.

By the way, in the case of aqueous plasters containing a water-soluble drug, the drug is solubilized in the adhesive base material by ionizing with an organic aqueous amine compound such as diisopropanol amine, when the drug is an acidic compound. Though possible, adoption of this technique in producing non-aqueous adhesives preparation containing the water-soluble drug, for example, solvent adhesives, which require a drying process, or hot melted type adhesive base materials, which require exposure to high temperature, may result in evaporation of moisture and thus crystallization of the drug in the adhesive base.

A surfactant may also be used as a component of the hot melted type adhesive base material in order to facilitate mixing of water. This approach, however, may cause skin irritation and thus is not favorable.

Aside from the above-described approaches, a water-absorbable or water-soluble high molecular weight compound is thought to enable the adhesive material to absorb water. One disadvantage of this approach is that moisture evaporates when the temperature is raised to melt the successive adhesive in continuous production. As a result, the high molecular weight compound crystallizes and forms unwanted particles in the adhesive base. Moreover, water is surrounded by the high molecular weight compound which is presented in the adhesive base material, and this prevents diffusion of the drug, i.e., the active ingredient, in the adhesive preparation, and as a result, the efficiency of the drug utilization is lowered.

Accordingly, it is an objective of the present invention to provide external plasters using an aqueous hot melted type adhesive base material which stably contains the active ingredient and exhibits a good releasability of the drug from the adhesive base material, thereby enhancing bioavailability of the drug based on the percutaneous absorption.

SUMMARY OF THE INVENTION

The present invention has been devised to overcome the above-described problems and provides in one aspect an external plaster using an aqueous hot melted type adhesive base material comprises as essential components a styrene-isoprene-styrene block copolymer, an adhesive resin, an antioxidant, lanolin, and water.

More specifically, the present invention provides an external plaster using above-mentioned aqueous adhesive base material, wherein an active ingredient to be percutaneously absorbed is contained in said adhesive base material.

In one preferred embodiment of the present invention, the external plaster contains water in an amount of 0.1 to 30%.

In summary, what is characteristic of the present invention resides containing an water-soluble drug in the hot melted type adhesive base material that contains a styrene-isoprene-styrene block copolymer, an adhesive resin, an antioxidant, lanolin and water as essential components. The plaster using said aqueous hot melted type adhesive base material has enhanced drug stability as well as enhanced drug releasability over time and thus overcomes the aforementioned drawbacks of the conventional art.

BEST MODE FOR CARRYING OUT THE INVENTION

An external plaster in accordance with the present invention will now be described in detail with the emphasis on the types and the amounts of the components contained.

Lanolin for use in the plaster of the present invention is also called "wool fat" and is purified and collected when secretions of sheep are washed off of wool. Lanolin is a cholesterin fat that does not lose its ointment-like viscosity even when added with 2 to 3 times as much water and is readily soluble in ether, chloroform, petroleum, benzine, or the like.

What is characteristic of the plaster of the present invention resides in the use of lanolin as a component of the adhesive base material for the plaster.

Styrene-isoprene-styrene block copolymer (hereinafter referred simply as to "SIS") for use in the plaster of the present invention is synthetic rubber to form the basic component of the adhesive base material and has ratio of styrene/rubber as 14/86. While adhesive base materials containing SIS are normally produced by melting at temperatures of 120 to 160° C., it is essential to design the production process of the aqueous hot melted type adhesive base material of the present invention so that the components are kneaded and mixed at about 90° C. in order to permit mixing of water.

It is thus preferred that the amount of SIS to be used is from 10 to 25% (as measured in % by weight with respect to the total weight of the adhesive preparation. All of the numbers expressed in percentages appear in the following description are calculated in the same manner.), more preferably from 15 to 25%. If the amount is less than 10%, the cohesion of the adhesive material is lost and it tends to remain on the surface to which it is applied after the plaster has been removed. In comparison, if the amount exceeds 25%, the adhesive base material becomes hard, making kneading and mixing of the adhesive base material difficult. As a result, the adhesion of the base material is reduced.

Adhesion resin for use in the plaster of the present invention may be any of the following resin materials such as aromatic resins, aliphatic resins, alicyclic petroleum resins, rosin resins, rosin ester resins and terpene resins.

The amount of the adhesive resin to be used is preferably from 15 to 35%, and more preferably from 20 to 30%. If the amount is less than 15%, then the adhesive base material can hardly exhibit the adhesion, and the cohesion of the adhesive base material is reduced. As a result, the base material tends to remain on the surface to which it is applied after the plaster has been removed. In comparison, if the amount exceeds 35%, the adhesive base material becomes hard, making kneading and mixing of the adhesive difficult. As a result, the adhesiveness of the base material is reduced.

Antioxidant for use in the plaster of the present invention is contained for the purpose of preventing the adhesive base material from undergoing deterioration due to oxidation during mixing and storage of the adhesive base material. Examples of the antioxidant include dibutylhydroxytoluene, pentaerythrityl-tetrakis [3-(3,5-di-t-butyl-4-hydroxyphenyl)]propionate, and tocopherol acetate. Preferably, these antioxidants are added in an amount of 0.1 to 2%.

Lanoline is used to serve not only to retain moisture in the adhesive base material but also as a softener of the adhesive base material. The amount of lanolin to be used is determined based on the balance between the amount of water and the amounts of other oils and fats and the softeners such as liquid rubbers. Preferably, the amount of lanolin is from 5 to 40% and more preferably from 10 to 30%. Lanolin contained in an amount less than 5% is insufficient for stable retention of water, whereas when contained in an amount greater than 40%, it makes the adhesive base material unfavorably sticky.

Water is contained for the purposes of dissolving a drug, i.e., an active ingredient and providing the base material with a sense of "cooling effect". The amount of water is determined based on the balance between the amount of the active ingredient and the amount of lanolin and is preferably from 0.1 to 30% and more preferably from 0.3 to 20%. If the amount of water is less than 0.1%, it becomes difficult not only to dissolve the drug in the base material but also to provide the "cooling effect" to the plaster. In comparison, the adhesive preparation can hardly have required properties if the amount of water exceeds 30%.

The drugs to be used in the external plaster of the present invention may be percutaneously absorbable and water-soluble drugs, and not limited those drugs. Examples include analgesic and anti-inflammatory, depressor, diuretic, anti-allergic, anti-asthmatic, coronaria vasodilator, bronchodilator, â-blocker and the like.

Examples of analgesic and anti-inflammatory drugs may include methyl salicylate, glycol salicylate, indometacin, ketoprofen, flurbiprofen, ibuprofen, diclofenac sodium, mefenamic acid, flufenamic acid, ibufenac, acrofenac, loxoprofen, piroxicam, naproxen, oxaprozin, silindac, felbinac (4-biphenyly acetic acid; hereinafter referred simply as to "BPAA"), and the like.

Examples of depressor may include clonidine, clonidine hydrochloride, atenolol, propranolol, propranolol hydrochloride, nicardipine hydrochloride, bupranolol, metoprolol tartrate, captopril, indenolol, nifedipine, and the like.

Further, examples of diuletic may include acetazolamide, potassium canrenoate, chlortalidone, spironolactone, trichlor-methiazide, flusemide, hydrochlorothiazide, hydroflumethiazide, and the like.

Examples of anti-allergic may include diphenhydramine hydrochloride, cyproheptadine hydrochloride, homochlorcyclizine hydrochloride, clemastine fumarate, chlorpheniramine maleate, mequitazine, and the like.

Examples of anti-asthmatic (antitussive) may include ephedrine hydrochloride, methylephedrine hydrochloride, pentoxyverine citrate, dextromethorphan hydrobromide, terbutaline sulfate, isoprenaline hydrochloride, and the like.

Examples of coronaria vasodilator may include nitroglycerin, nitroglycol, isosorbide nitrate, dipyridamole, molisidomine, and the like, and examples of bronchodilator may include trimetrquinol hydrochloride, procaterol hydrochloride, mabuterol hydrochloride, salbutamol sulfate, theophylline, tulobuterol and the like.

The plaster of the present invention may optionally contain a pharmaceutically acceptable absorption enhancer, refrigerant, preservative, bactericide, pigment and other pharmaceutically acceptable agents as desired.

Using the above-described adhesive components, the external plaster of the present invention can be manufactured, for example, through the following process.

For example, SIS, the adhesive resin, the antioxidant, lanolin, and the softener are melted, mixed, and kneaded in a kneader heated to about 150° C. to obtain the adhesive base material, which is then cooled to 90° C. by air or water.

Subsequently, warm water, together with a drug solution (aqueous) to serve as the active ingredient solution, is added gradually to the adhesive base material under stirring. The resulting adhesive base material is spread on the liner to a predetermined thickness, and then, laminated with the backing. Then, the backing thus obtained is cut into desired size to produce the plaster of the present invention.

Alternatively, the adhesive base material may be prepared in a separate container and is stored into block forms. A required amount of the block forms is then melted at about 90° C. and mixed with water and the active ingredient solution.

If the temperature of the adhesive base material exceeds 100° C. during addition of the aqueous solution of the active ingredient and water, water is brought to boiling and evaporates, and as a result, the amount of water in the plaster is significantly reduced. In comparison, if the temperature is lower than 80° C., the adhesive base material becomes so viscous that it is difficult to stir the mixture during the addition of the aqueous solution of the active ingredient. This prevents uniform dispersion of the active ingredient.

EXAMPLES

The present invention will be further illustrated by the following examples. It is to be understood that the present invention is not limited to these examples. Details may be deleted, added, or substituted as it is deemed to be appropriate, so long as the pharmacological activities of the plaster of the present invention is not changed. Such changes are also covered within the technical scope of the present invention. Thus the temperature at the adding and mixing of the aqueous solution must be 80 to 100° C.

Examples 1 to 5

BPAA, an analgesic and anti-inflammatory drug was used for the active ingredient of these examples. Adhesive base materials with formulations shown in Tables 1 below were prepared.

A sheet of polyester film treated with silicone was used to serve as a liner, and a piece of fabric made from polyester fiber was used to serve as a backing for each adhesive base material. The amount of each adhesive base material coated was 100 g/m$^2$.

TABLE 1

Formulations of adhesive base material of example 1 to 5

| Materials | Ex. 1 | Ex. 2 | Ex. 3 | Ex. 4 | Ex. 5 |
|---|---|---|---|---|---|
| SIS | 14.0 | 18.0 | 16.0 | 17.0 | 16.0 |
| Saturated alicyclic petroleum resin | 25.0 | — | — | — | — |
| Rosin ester resin | — | 22.0 | — | — | — |
| Terpene resin | — | — | 24.0 | 25.0 | 24.0 |
| Polybutene | — | — | 7.0 | 19.0 | 6.0 |
| Liquid paraffin | 13.0 | 6.0 | 17.0 | 8.0 | — |
| Polyethyleneglycol-400 | — | — | 10.0 | 5.0 | — |
| Dibutylhydroxytoluene | 1.0 | 1.0 | 1.0 | 1.0 | 1.0 |
| Lanolin | 24.0 | 25.0 | 10.0 | 10.0 | 25.0 |
| Purified water | 9.0 | 9.0 | 1.0 | 1.0 | 9.0 |
| Purified water (solvent for the BPAA) | 1.0 | 1.0 | 1.0 | 1.0 | 1.0 |
| Diisopropanolamine | 5.0 | 5.0 | 5.0 | 5.0 | 10.0 |
| Crotamiton | 2.5 | 2.5 | 2.5 | 2.5 | 2.5 |
| BPAA | 5.0 | 5.0 | 5.0 | 5.0 | 5.0 |
| 1-menthol | 0.5 | 0.5 | 0.5 | 0.5 | 0.5 |
| Isopropyl myristate | — | 5.0 | — | — | — |

Comparative Examples 1 to 4

As Comparative Examples, external plaster using water-free hot melted type adhesives base material and commercially available acrylic acid ester adhesives were prepared. Formulation for each Comparative Example is shown in Table 2 below.

TABLE 2

Formulations of adhesive base material for Comparative Examples (Comp. 1 to 4)

| Materials | Comp. 1 | Comp. 2 | Comp. 3 | Comp. 4 |
|---|---|---|---|---|
| SIS | 18.0 | 20.0 | — | — |
| Terpene resin | 29.0 | 31.0 | — | — |
| Polybutene | 15.0 | 15.0 | — | — |
| Liquid paraffin | 9.0 | 15.0 | — | — |
| Polyethyleneglycol-400 | 5.0 | 5.0 | 5.0 | 5.0 |
| Dibutylhydroxytoluene | 1.0 | 1.0 | — | — |
| Acrylic adhesive A *[1] | — | — | 72.0 | — |
| Acrylic adhesive B *[2] | — | — | — | 72.0 |
| Lanolin | 10.0 | — | 10.0 | 10.0 |
| Diisopropanolamine | 5.0 | 5.0 | 5.0 | 5.0 |
| Crotamiton | 2.5 | 2.5 | 2.5 | 2.5 |
| BPAA | 5.0 | 5.0 | 5.0 | 5.0 |
| 1-menthol | 0.5 | 0.5 | 0.5 | 0.5 |

*[1] 2-ethylhexyl acrylate/vinyl acetate copolymer (commercially available)
*[2] 2-ethylhexyl acrylate/vinyl pyrrolidone copolymer (commercially available)

Test Example 1

Drug Permeability Test

Using a commercially available aqueous BPAA plaster (cataplasm) as a control, the above-prepared plasters of Examples and Comparative Examples were tested for the ability to permeate the drug component in the in vitro skin permeability tests.

Methods:

Using a scalpel and scissors, a piece of abdominal skin was cut from a hairless rat and was mounted on a vertically placed Franz diffusion cell with the receptor compartment filled with saline. Warm water with a temperature of about 35° C. was circulated through the jacket of the cell.

The above-prepared plasters were each applied to the skin of hairless rat, and the receptor solution was sampled over time for each plaster. The amount of the drug permeated in 24 hours was determined by HPLC.

Results:

The results of the tests are shown in Table 3. For the commercially available aqueous BPAA plaster (cataplasm) serving as the control, the amount of the permeated drug was 66.0 ig/cm$^2$.

TABLE 3

Results of rat skin permeability test

| Plaster No. | Ex. 1 | Ex. 2 | Ex. 3 | Ex. 4 | Ex. 5 |
|---|---|---|---|---|---|
| Amount permeated ig/cm$^2$ | 58.2 | 174.6 | 62.4 | 81.5 | 65.8 |

| Plaster No | Comp. 1 | Comp. 2 | Comp. 3 | Comp. 4 |
|---|---|---|---|---|
| Amount permeated ig/cm$^2$ | 29.8 | 21.5 | 43.7 | 31.6 |

As can be seen from the results of Table 3 above, the plaster of Examples of the present invention each exhibited higher skin permeability than the plaster of Comparative Examples. This indicates that the plaster of the present invention has an improved releasability of the drug.

Test Example 2

Stability Test

The above-prepared plasters of Examples and Comparative Examples were each placed in a polyethylene-aluminum bag, were stored for 6 months at 40° C., and were then examined for the presence of crystal deposition.

No crystal deposition was observed on the plasters of Examples, whereas crystals formed on the plasters of Comparative Examples as early as after 1 month, causing the plasters to remain stuck to the liner and significantly reducing the adhesion. No decrease was observed in the amount of the active ingredient (BPAA) in any of the preparations.

The presence or the absence of crystal deposition on the plasters observed after the storage period was shown in Tables 4 and 5, with the results of the adhesive strength of the plasters.

The adhesive strength (unit=g/25 mm) was measured by peeling the plaster from a Bakelite plate at 180° angles.

TABLE 4

Results of stability test (Examples 1 to 5)

|  |  | Ex. 1 | Ex. 2 | Ex. 3 | Ex. 4 | Ex. 5 |
|---|---|---|---|---|---|---|
| Initial (after production) | Crystal | None | None | None | None | None |
|  | Adhesive strength | 780 | 890 | 540 | 690 | 750 |
| 40° C. 1 month | Crystal | None | None | None | None | None |
|  | Adhesive strength | 750 | 870 | 610 | 710 | 770 |
| 40° C. 3 months | Crystal | None | None | None | None | None |
|  | Adhesive strength | 760 | 890 | 590 | 680 | 730 |
| 40° C. 6 months | Crystal | None | None | None | None | None |
|  | Adhesive strength | 740 | 790 | 620 | 690 | 750 |

TABLE 5

Results of stability test (Comparative Examples 1 to 4)

|  |  | Comp. 1 | Comp. 2 | Comp. 3 | Comp. 4 |
|---|---|---|---|---|---|
| Initial (after production) | Crystal | None | None | None | None |
|  | Adhesive strength | 2340 | 1780 | 2540 | 1520 |
| 40° C. 1 month | Crystal | formed | formed | formed | Formed |
|  | Adhesive strength | 1580 | 320 | 410 | 280 |
| 40° C. 3 months | Crystal | formed | formed | formed | Formed |
|  | Adhesive strength | 1460 | 380 | 340 | 250 |
| 40° C. 6 months | Crystal | formed | formed | formed | Formed |
|  | Adhesive strength | 1390 | 350 | 390 | 280 |

Examples 6 and 7

External Plaster Containing Salbutamol Sulfate and Propranolol Hydrochloride

Salbutamol sulfate as bronchodilator, and proprnolol hydrochloride as a-broker for treatment of angina were used for the active ingredient of these examples. Adhesive base materials with formulations shown in Tables 6 below were prepared.

A sheet of polyester film treated with silicone was used to serve as a liner, and a piece of fabric made from polyester fiber was used to serve as a backing for each adhesive base material. The amount of each adhesive base material coated was 100 g/m$^2$.

TABLE 6

Formulations of adhesive base material of examples 6 and 7

| Materials | Ex. 1 | Ex. 2 |
|---|---|---|
| SIS | 22.0 | 20.0 |
| Saturated alicyclic petroleum resin | 25.0 | 25.0 |
| Polybutene | 8.0 | 7.0 |
| Lanolin | 20.0 | 250 |
| Polyethyleneglycol-400 | 3.0 | 3.0 |
| Crotamiton | 2.0 | 2.0 |
| Dibutylhydroxytoluene | 1.0 | 1.0 |
| Diethyl sebacate | 3.0 | — |
| Oleic acid | — | 1.0 |
| Purified water | 10.0 | 10.0 |
| Salbutamol sulfate (Active ingredient) | 6.0 | — |
| propranolol hydrochloride (Active ingredient) | — | 6.0 |

Test Example 3

Drug Permeability Test

The above-prepared plasters of Examples 6 and 7 were tested for the ability to permeate the drug component in the in vitro skin permeability tests.

Methods:

Using a scalpel and scissors, a piece of abdominal skin was cut from a hairless rat (6 rats for each groups) and was mounted on a vertically placed Franz diffusion cell with the receptor compartment filled with saline. Warm water with a temperature of about 35° C. was circulated through the jacket of the cell.

The above-prepared plasters were each applied to the skin of hairless rat, and the receptor solution was sampled over time for each plaster. The amount of the drug permeated at 2, 4, 6, 8 and 24 hours after administration was determined by HPLC.

Results:

The results of the tests are shown in Table 7.

TABLE 7

Results of rat skin permeability test

Rat skin permeability test for plaster containing salbutamol sulfate (Example 6)
Drug amount permeated at each times (ig/cm$^2$)

| Time | 0 | 2 | 4 | 6 | 8 | 24 |
|---|---|---|---|---|---|---|
| Amount | 0 | 2.17 | 3.18 | 5.56 | 7.29 | 20.9 |

Rat skin permeability test for plaster containing propranolol hydrochloride (Example 7)
Drug amount permeated at each times (ig/cm$^2$)

| Time | 0 | 2 | 4 | 6 | 8 | 24 |
|---|---|---|---|---|---|---|
| Amount | 0 | 2.41 | 9.84 | 19.27 | 25.82 | 59.76 |

As can be seen from the results of Table 7 above, the plaster of Examples of the present invention each exhibited higher skin permeability and good releasability of the drug.

INDUSTRIAL APPLICABILITY

As mentioned above, the external plaster of the present invention, which is using an aqueous hot melted type adhesive base material comprising as essential components a styrene-isoprene-styrene block copolymer, an adhesive resin, an antioxidant, lanolin, and water, is advantageous in that it exhibits a good drug stability as well as a good drug releasability over time and the adhesion of the plaster is not decreased over time.

What is claimed is:

1. A external plaster using an aqueous hot melted type adhesive base material comprising a styrene-isoprene-styrene block copolymer an adhesive resin, an antioxidant, lanolin, and water, in the absence of a hydrophilic polymer.

2. The external plaster according to claim 1, wherein the water is present in a range of 0.1 to 30%.

3. The external plaster according to claim 1, wherein an active ingredient to be percutaneously absorbed is contained in the aqueous hot melted type adhesive base material.

4. The external plaster according to claim 2, wherein an active ingredient to be percutaneously absorbed is contained in the aqueous hot melted type adhesive base material.

5. The external plaster according to claim 1, wherein the styrene-isoprene-styrene block copolymer is present in an amount of 10 to 25% by weight.

6. The external plaster according to claim 5, wherein the styrene-isoprene-styrene block copolymer is present in an amount of 15 to 25 % by weight.

7. The external plaster according to claim 1, wherein the adhesive resin is selected from the group consisting of aromatic resins, aliphatic resins, alicyclic petroleum resins, rosin resins, rosin ester resins and terpene resins.

8. The external plaster according to claim 1, wherein the adhesive resin is present in an amount of from 15 to 35% by weight.

9. The external plaster according to claim 8, wherein the adhesive resin is present in an amount of from 20 to 30% by weight.

10. The external plaster according to claim 1, wherein the antioxidant is selected from the group consisting of dibutylhydroxytoluene, pentaerythrityl-tetrakis[3-(3,5-di-t-butyl-4-hydroxyphenyl)]propionate, and tocopherol acetate.

11. The external plaster according to claim 1, wherein the antioxidant is present in an amount of 0.1 to 2% by weight.

12. The external plaster according to claim 1, wherein the lanolin is present in an amount of from 5 to 40% by weight.

13. The external plaster according to claim 12, wherein the lanolin is present in an amount of from 10 to 30% by weight.

14. The external plaster according to claim 2, wherein the water is present in an amount of from 0.3 to 20% by weight.

15. An external plaster using an aqueous hot melted type adhesive base material consisting essentially of a styrene-isoprene-styrene block copolymer, an adhesive resin, an antioxidant, lanolin, and water.

16. The external plaster according to claim 15, wherein the water is present in a range of 0.1 to 30%.

17. The external plaster according to claim 15, wherein an active ingredient to be percutaneously absorbed is contained in the aqueous hot melted type adhesive base material.

18. The external plaster according to claim 16, wherein an active ingredient to be percutaneously absorbed is contained in the aqueous hot melted type adhesive base material.

19. The external plaster according to claim 15, wherein the styrene-isoprene-styrene block copolymer is present in an amount of 10 to 25% by weight.

20. The external plaster according to claim 19, wherein the styrene-isoprene-styrene block copolymer is present in an amount of 15 to 25% by weight.

21. The external plaster according to claim 15, wherein the adhesive resin is selected from the group consisting of aromatic resins, aliphatic resins, alicyclic petroleum resins, rosin resins, rosin ester resins and terpene resins.

22. The external plaster according to claim 15, wherein the adhesive resin is present in an amount of from 15 to 35% by weight.

23. The external plaster according to claim 22, wherein the adhesive resin is present in an amount of from 20 to 30% by weight.

24. The external plaster according to claim 15, wherein the antioxidant is selected from the group consisting of dibutylhydroxytoluene, pentaerythrityl-tetrakis[3-(3,5-di-t-butyl-4-hydroxyphenyl)]propionate, and tocopherol acetate.

25. The external plaster according to claim 15, wherein the antioxidant is present in an amount of 0.1 to 2% by weight.

26. The external plaster according to claim 15, wherein the lanolin is present in an amount of from 5 to 40% by weight.

27. The external plaster according to claim 26, wherein the lanolin is present in an amount of from 10 to 30% by weight.

28. The external plaster according to claim 16, wherein the water is present in an amount of from 0.3 to 20% by weight.

29. A process for producing an aqueous hot melted type adhesive base material, which comprises melting and kneading a styrene-isoprene-styrene block copolymer, an adhesive resin, an antioxidant, lanolin, and water, in the absence of a hydrophilic polymer, at a temperature at which the water will not boil.

30. The process according to claim 29, wherein said styrene-isoprene-styrene block copolymer, adhesive resin, antioxidant, lanolin, and water are kneaded at a temperature of 80 to 100° C.

31. The process according to claim 30, wherein said styrene-isoprene-styrene block copolymer, adhesive resin, antioxidant, lanolin, and water are kneaded at a temperature of about 90° C.

32. The process according to claim 29, wherein said styrene-isoprene-styrene block copolymer, adhesive resin, antioxidant, and lanolin are mixed and kneaded in a kneader heated to about 150° C. and then cooled.

33. The process according to claim 32, further comprising adding warm water and an aqueous solution of an active ingredient to be percutaneously absorbed after said cooling step.

34. A process for producing an aqueous hot melted type adhesive base material, comprising melting and kneading ingredients consisting essentially of a styrene-isoprene-styrene block copolymer, an adhesive resin, an antioxidant, lanolin, and water at a temperature at which the water will not boil.

35. The process according to claim 34, wherein said styrene-isoprene-styrene block copolymer, adhesive resin, antioxidant, lanolin, and water are kneaded at a temperature of 80 to 100° C.

36. The process according to claim 35, wherein said styrene-isoprene-styrene block copolymer, adhesive resin, antioxidant, lanolin, and water are kneaded at a temperature of about 90° C.

37. The process according to claim 34, wherein said styrene-isoprene-styrene block copolymer, adhesive resin, antioxidant, and lanolin are mixed and kneaded in a kneader heated to about 150° C. and then cooled.

38. The process according to claim 37, including the step of adding warm water and an aqueous solution of an active ingredient to be percutaneously absorbed after said cooling step.

* * * * *